United States Patent
Saxena

(10) Patent No.: US 6,423,515 B1
(45) Date of Patent: Jul. 23, 2002

(54) METHODS OF MAKING NUCLEIC ACIDS ENCODING RIBONUCLEASES

(75) Inventor: Shailendra K. Saxena, West Orange, NJ (US)

(73) Assignee: Alfacell Corporation, Bloomfield, NJ (US)

( * ) Notice: Subject to any disclaimer, the term of this patent is extended or adjusted under 35 U.S.C. 154(b) by 0 days.

(21) Appl. No.: 09/687,748

(22) Filed: Oct. 14, 2000

Related U.S. Application Data

(62) Division of application No. 09/394,268, filed on Sep. 10, 1999, now Pat. No. 6,175,003.
(51) Int. Cl.[7] ............................................. C12P 19/34
(52) U.S. Cl. ..................... 435/91.1; 435/91.2; 435/69.1; 435/320.1
(58) Field of Search ............................... 435/91.1, 91.2, 435/69.1, 320.1

(56) References Cited

PUBLICATIONS

Boix et al. Journal ov Molecular Biology (1996) 257, 992–1007.*

* cited by examiner

Primary Examiner—Jeffrey Fredman
Assistant Examiner—Juliet Einsmann

(57) ABSTRACT pET11d-rOnc(Q1, M23L) DNA is subjected to two different site-directed mutations, each using an overlapping PCR protocol. One of the site-directed mutations changes the amino acid residue at position 23 of the encoded protein from leucine to methionine, whereby the encoded protein can be made into ranpirnase by cleaving the N-terminal methionine residue and allowing the adjacent glutamine residue to autocyclize. The other site-directed mutation changes the amino acid residue at position 72 of the encoded protein from serine to cysteine, thereby producing an encoded protein that can be made into a cysteinized ranpirnase by cleaving the N-terminal methionine residue and allowing the adjacent glutamine residue to autocyclize.

7 Claims, 2 Drawing Sheets

SEQUENCE LISTING

<160> NUMBER OF SEQ ID NOS: 8

<210> SEQ ID NO 1
<211> LENGTH: 104
<212> TYPE: PRT
<213> ORGANISM: Rana pipiens

<400> SEQUENCE: 1

```
Gln Asp Trp Leu Thr Phe Gln Lys Lys His Ile Thr Asn Thr Arg Asp
 1               5                  10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100
```

<210> SEQ ID NO 2
<211> LENGTH: 104
<212> TYPE: PRT
<213> ORGANISM: Artificial Sequence
<220> FEATURE:
<223> OTHER INFORMATION: SEQ ID NO:1 with Leu at position 23 and Cys at
      position 72

<400> SEQUENCE: 2

```
Gln Asp Trp Leu Thr Phe Gln Lys Lys His Ile Thr Asn Thr Arg Asp
 1               5                  10                  15

Val Asp Cys Asp Asn Ile Leu Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Cys Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100
```

<210> SEQ ID NO 3
<211> LENGTH: 43
<212> TYPE: DNA
<213> ORGANISM: Artificial Sequence
<220> FEATURE:
<223> OTHER INFORMATION: Forward PCR Primer containing Xba1 site

<400> SEQUENCE: 3
caattcccct ctagaaataa ttttgtttaa ctttaagaag gag                            43

<210> SEQ ID NO 4

-continued

```
<211> LENGTH: 32
<212> TYPE: DNA
<213> ORGANISM: Artificial Sequence
<220> FEATURE:
<223> OTHER INFORMATION: Reverse PCR Primer containing BamH1 site

<400> SEQUENCE: 4
cgcgcggatc cctactagca agaaccaaca cc                              32

<210> SEQ ID NO 5
<211> LENGTH: 39
<212> TYPE: DNA
<213> ORGANISM: Artificial Sequence
<220> FEATURE:
<223> OTHER INFORMATION: Mutated Forward PCR Primer to produce SEQ ID
      NO:1

<400> SEQUENCE: 5
gactgcgaca acatcatgtc tactaacctg ttccattgc                       39

<210> SEQ ID NO 6
<211> LENGTH: 39
<212> TYPE: DNA
<213> ORGANISM: Artificial Sequence
<220> FEATURE:
<223> OTHER INFORMATION: Mutated Reverse PCR Primer to produce SEQ ID
      NO:1

<400> SEQUENCE: 6
gaacaggtta gtagacatga tgttgtcgca gtcaacgtc                       39

<210> SEQ ID NO 7
<211> LENGTH: 39
<212> TYPE: DNA
<213> ORGANISM: Artificial Sequence
<220> FEATURE:
<223> OTHER INFORMATION: Mutated Forward PCR Primer to produce SEQ ID
      NO:2

<400> SEQUENCE: 7
gactgcaacg ttacttgccg tccgtgcaaa tacaaactg                       39

<210> SEQ ID NO 8
<211> LENGTH: 39
<212> TYPE: DNA
<213> ORGANISM: Artificial Sequence
<220> FEATURE:
<223> OTHER INFORMATION: Mutated Reverse PCR Primer to produce SEQ ID
      NO:2

<400> SEQUENCE: 8
gtatttgcac ggacggcaag taacgttgca gtcagacag                       39
```

METHODS OF MAKING NUCLEIC ACIDS ENCODING RIBONUCLEASES

This is a divisional of application Ser. No. 09/394,268, filed Sep. 10, 1999, now U.S. Pat. No. 6,175,003 B1.

Background of the Invention

The invention relates to Ribonucleases (RNases), and more particularly relates to ranpirnase. In its most immediate sense, the invention relates to nucleic acids that encode proteins that can be used to produce ranpirnase and an RNase that is highly homologous to it.

Ranpirnase is the generic name of an RNase that is produced by Alfacell Corporation (assignee herein) under the registered trademark ONCONASE. Ranpirnase is a protein 104 residues long, with a blocked N-terminal of pyroglutamic acid (<Glu) that is produced by autocyclization of glutamine (Gln). It is disclosed in U.S. Pat. No. 5,519,212. As is stated therein, ranpirnase is presently produced from eggs of the rana pipiens frog. It would be advantageous to produce ranpirnase using recombinant DNA technology instead of processing biological material.

Additionally, work done at the direction of Dr. Richard Youle of the National Institute of Health has suggested that there would be an advantage to modifying ranpirnase in a particular manner. Dr. Youle is a pioneer in the field of "cysteinizing" therapeutically active RNases (specifically, human pancreatic RNase) with the object of increasing their effectiveness. Dr. Youle conceived the idea of re-engineering an RNase so it could be more easily attached to a targeting molecule, thereby making it possible for the RNase to be delivered to a particular cell receptor where it might be most effective. To achieve this objective, he utilized a property of the amino acid cysteine.

Cysteine has a single reactive sulhydryl ("SH") group. The availability of this group facilitates the chemical linking of a targeting molecule to the cysteine residue. Dr. Youle realized that by conservatively substituting a cysteine residue at an appropriate location in an RNase, the RNase could easily be linked to a targeting moiety (such as a monoclonal antibody) that targets a predetermined cell receptor. This would permit the RNase to be delivered to the precise location where it might be most therapeutically effective.

Accordingly, it would be advantageous to produce a cysteinized ranpirnase, i.e. a modified ranpirnase in which an amino acid residue at an appropriate location was conservatively replaced by cysteine.

One object of the invention is to provide a nucleic acid that encodes ranpirnase, and to provide a method of synthesizing that nucleic acid.

Another object of the invention is to provide a nucleic acid that encodes cysteinized ranpirnase, and to provide a method of synthesizing that nucleic acid.

In accordance with the invention, two nucleic acids are produced. Each of these nucleic acids encodes a corresponding protein. One protein is converted to ranpirnase by cleavage of an N-terminal methionine residue at position −1 and autocyclization of a glutamine residue at position 1. The other protein (after a like cleavage and autocyclization) is converted to a cysteinized ranpirnase in which the methionine residue at position 23 is replaced by a residue of leucine, and in which the serine residue at position 72 is replaced by a residue of cysteine. (The substitution of methionine at position 23 does not appear to adversely affect the bioactivity of the resulting RNase.) The cysteine residue provides a location at which a targeting moiety (such as a monoclonal antibody) can be attached, to deliver the cysteinized ranpirnase to that receptor site where it can most efficiently be used.

In accordance with preferred embodiments of the invention, synthesis of both nucleic acids begins with a recombinant plasmid originally synthesized in Dr. Youle's laboratory. This recombinant plasmid, named pET11d-rOnc (Q1, M23L) and made up of a rOnc(Q1, M23L) gene cloned in a pET-11d vector, encodes a protein. The protein is highly homologous to ranpirnase, but a) has an N-terminal residue of methionine at position −1 followed by a residue of glutamine at position 1, and b) has a leucine residue at position 23 instead of a methionine residue (as ranpirnase has). An overlapping PCR protocol is used to mutate the rOnc(Q1, M23L) gene. In accordance with a first preferred embodiment of the invention, the rOnc(Q1, M23L) gene is modified to encode a protein that, after cleavage of its N-terminal methionine residue and autocyclization of an adjacent glutamine residue, is ranpirnase. In accordance with a second preferred embodiment of the invention, the rOnc(Q1, M23L) gene is modified to encode a protein that, after a like cleavage and autocyclization, is a cysteinized ranpirnase wherein the leucine residue at position 23 is left in place and the serine residue at position 72 is changed to a residue of cysteine.

The expressed protein from each of these preferred embodiments has an N-terminal residue of methionine at position −1 followed by a residue of glutamine at position 1. When in each instance the methionine residue is cut off (or "cleaved"), the glutamine autocyclizes to form pyroglutamic acid (which is also located at position 1 in ranpirnase).

BRIEF DESCRIPTION OF THE DRAWINGS

The invention will be better understood with the aid of the following illustrative and non-limiting drawings, in which.

DETAILED DESCRIPTION OF PREFERRED EMBODIMENTS

Figure 1:
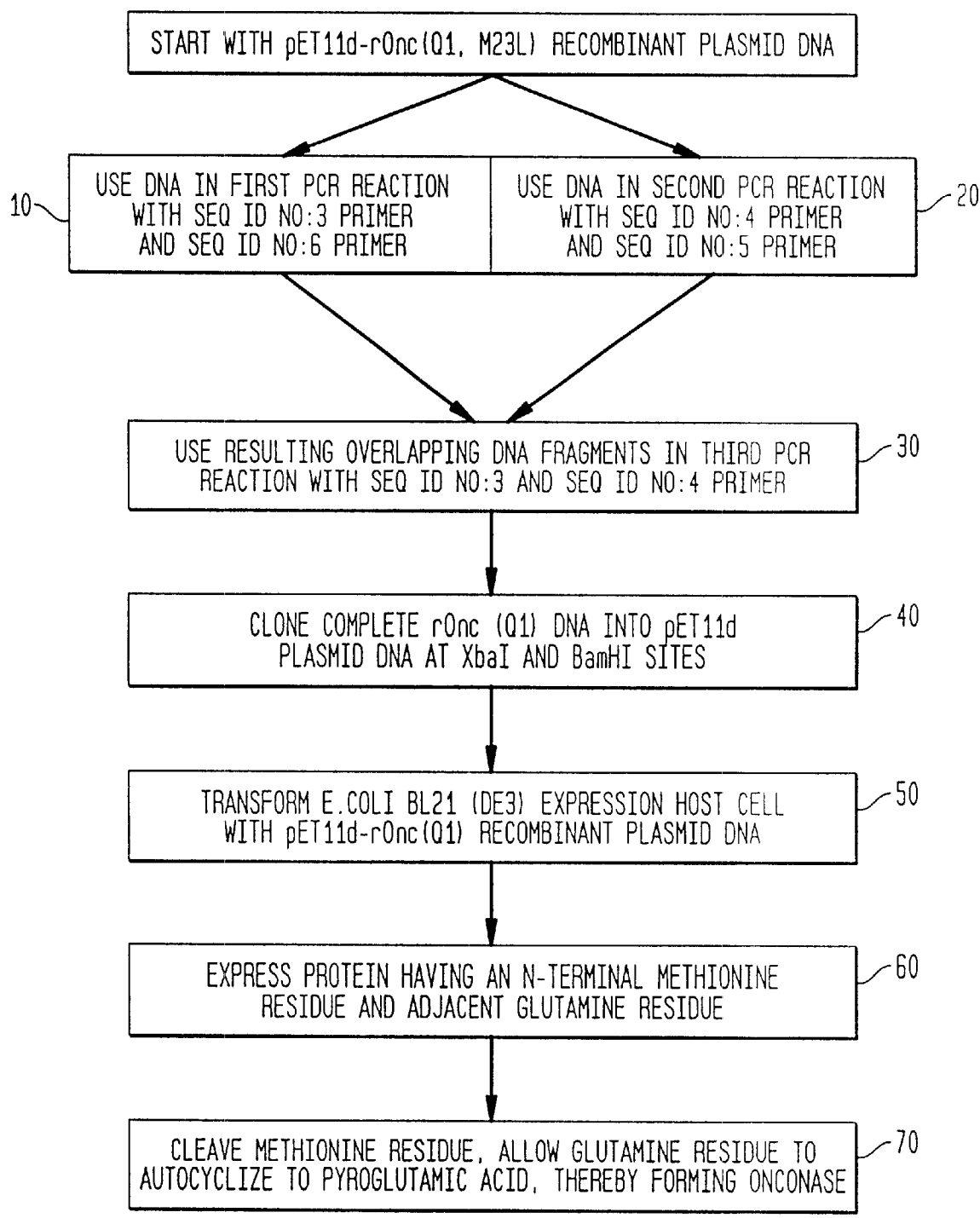
FIG. 1 is a flowchart showing a first preferred embodiment of the invention.

Ranpirnase, known by the trademark ONCONASE and presently undergoing clinical trials, has an amino acid sequence that is 104 residues long and that has pyroglutamic acid (<Glu) at its N-terminal. The pyroglutamic acid is produced by autocyclization of glutamine (Gln) after the removal of a residue of methionine (Met) at position −1. For this reason, the amino acid sequence of ranpirnase is herein shown as SEQ ID NO:1.

A recombinant plasmid named pET11d-rOnc(Q1, M23L) and made up of the rOnc(Q1,M23L) gene cloned in a pET-11d vector, encodes a protein that has an N-terminal methionine residue at position −1, a residue of glutamine at position 1, and that from position 2 on has the same amino acid sequence as ranpirnase, except that in the encoded protein the methionine residue at position 23 is changed to a residue of leucine. (This recombinant plasmid was synthesized by YouNeng Wu in the laboratory of Dr. Richard J. Youle, and is described in *J. Mol. Biol.* (1996) 257, 992–1007.) In accordance with a first preferred embodiment of the invention as is described immediately below, the pET11d-rOnc(Q1, M23L) gene is modified using an overlapping PCR protocol that changes this position 23 leucine residue back to methionine (a "site-directed mutation").

Reagents from Perkin Elmer (Branchburg N.J.), Stratagene (La Jolla Calif.) and Novagen (Madison Wis.) were used for PCR and other recombinant DNA manipulations. The primers were designed to generate protein fragments having an XbaI site at the 5' end and a stop codon flanked by a BamHI site at the 3' end. (The use of primers that generate XbaI and BamHI sites are not necessary and are not part of the invention. These primers were chosen because the cloning vector is intended to be of pET-11d. If another vector were to be used, the XbaI and BamHI sites would be changed to the sites that are appropriate to that other vector.)

In accordance with this first preferred embodiment, four primers are constructed for use in an overlapping PCR protocol. These are a forward PCR primer, a reverse PCR primer, a mutated forward PCR primer, and a mutated reverse PCR primer, as follows: the forward PCR primer is SEQ ID NO:3, the reverse PCR primer is SEQ ID NO:4, the mutated forward PCR primer is SEQ ID NO:5, and the mutated reverse PCR primer is SEQ ID NO:6. The forward PCR primer contains an XbaI restriction site, the reverse PCR primer contains a stop codon followed by a BamHI restriction site. The mutated forward and reverse PCR primers are chosen to carry out a particular site-directed mutation, namely to change the leucine residue at position 23 to a residue of methionine.

In a first PCR reaction using Pfu DNA polymerase (FIG. 1, step 10), the recombinant plasmid pET11d-rOnc (Q1, M23L) DNA is used as a template with the forward PCR primer SEQ ID NO:3 and the mutated reverse PCR primer SEQ ID NO:6. In a second PCR reaction using Pfu DNA polymerase (FIG. 1, step 20), the recombinant plasmid pET11d-rOnc(Q1, M23L) DNA is used as a template with the reverse PCR primer SEQ ID NO:4 and the mutated forward PCR primer SEQ ID NO:5. These first and second PCR reactions produce overlapping DNA fragments that have the desired mutation (leucine residue to methionine residue at location 23) in their regions of overlap.

Then, in a third PCR reaction using Pfu DNA polymerase (FIG. 1, step 30), these overlapping DNA fragments are mixed together with the forward PCR primer SEQ ID NO:3 and the reverse PCR primer SEQ ID NO:4. This produces a full-length gene having an XbaI restriction site at one end and a BamHI restriction site at the other. This new gene has been named rOnc(Q1). The new rOnc(Q1) gene can then be cloned (FIG. 1, step 40) into a pET11d plasmid vector using the XbaI and BamHI restriction sites. The resulting pET11d-rOnc(Q1) recombinant plasmid is then used to transform an expression host cell (FIG. 1, step 50). An appropriate host cell is E.coli BL21(DE3). A protein is expressed from the host cell (FIG. 1, step 60). The expressed protein has an N-terminal methionine (Met) residue at position −1 followed by a residue of glutamine (Gln) at position 1. When the methionine residue is cleaved (FIG. 1, step 70) the glutamine autocyclizes to form pyroglutamic acid (<Glu), forming ranpirnase (SEQ ID NO:1).

In a second preferred embodiment of the invention, the gene in the pET11d-rOnc(Q1, M23L) recombinant plasmid DNA is subjected to a different site-directed mutation. In this other site-directed mutation, the amino acid residue at position 72 in the encoded protein is changed from serine (Ser) residue to cysteine (Cys) using different overlapping PCR primers. In this different overlapping PCR protocol, the forward and reverse PCR primers (i.e. the primers that have the XbaI and BamHI restriction sites) are the same as those used in the first preferred embodiment. However, the mutated forward and reverse PCR primers are different, because they change the serine residue at position 72 in the encoded protein to cysteine.

Hence, in accordance with this second preferred embodiment, four primers are constructed for use in an overlapping PCR protocol. These are a forward PCR primer, a reverse PCR primer, a mutated forward PCR primer, and a mutated reverse PCR primer, as follows: the forward PCR primer is SEQ ID NO:3, the reverse PCR primer is SEQ ID NO:4, the mutated forward PCR primer is SEQ ID NO:7, and the mutated reverse PCR primer is SEQ ID NO:8. As in the first preferred embodiment, the forward PCR primer contains an XbaI restriction site and the reverse PCR primer contains a stop codon followed by a BamHI restriction site. However, in this second preferred embodiment, the mutated forward and reverse PCR primers are chosen to carry out a different site-directed mutation in the encoded protein, namely a change of the residue at position 72 from serine to cysteine.

In a first PCR reaction using Pfu DNA polymerase (FIG. 2, step 80), the recombinant plasmid pET11d-rOnc(Q1, M23L) DNA is used as a template with the forward PCR primer SEQ ID NO:3 and the mutated reverse PCR primer SEQ ID NO:8. In a second PCR reaction using Pfu DNA polymerase (FIG. 2, step 90), the recombinant plasmid pET11d-rOnc(Q1, M23L) DNA is used as a template with the reverse PCR primer SEQ ID NO:4 and the mutated forward PCR primer SEQ ID NO:7. These first and second PCR reactions produce overlapping DNA fragments that have the desired mutation (serine residue to cysteine residue at location 72) in their regions of overlap.

Figure 2:
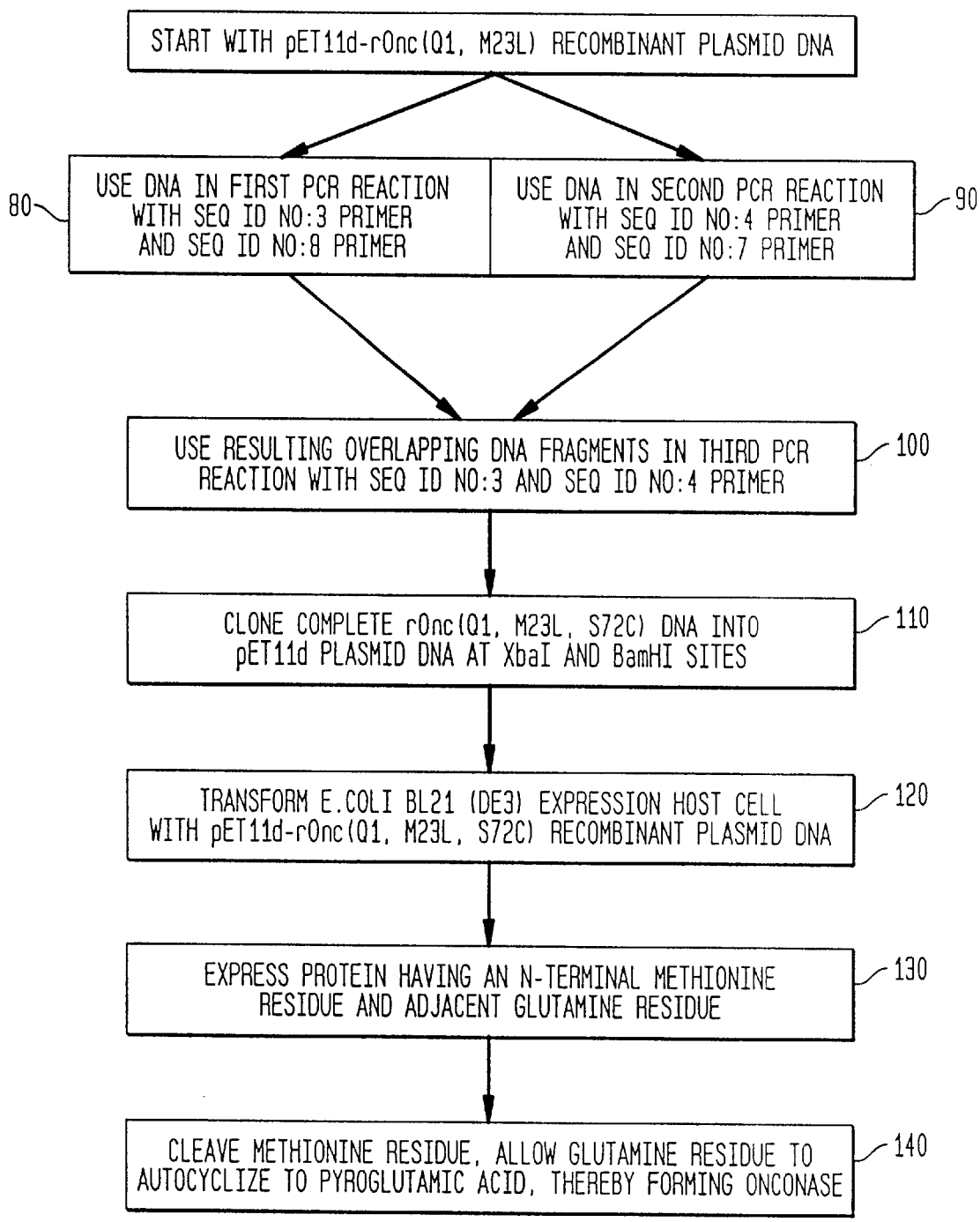
FIG. 2 is a flowchart showing a second preferred embodiment of the invention.

Then, in a third PCR reaction using Pfu DNA polymerase (FIG. 2, step 100), these overlapping DNA fragments are mixed together with the forward PCR primer SEQ ID NO:3 and the reverse PCR primer SEQ ID NO:4. This produces a full-length gene having an XbaI restriction site at one end and a BamHI restriction site at the other. This new gene has been named rOnc(Q1, M23L, S72C). The new rOnc (Q1, M23L, S72C) gene can then be cloned (FIG. 2, step 110) into a pET11d plasmid at the XbaI and BamHI restriction sites to produce a pET11d-rOnc (Q1, M23L, S72C) recombinant plasmid. The resulting pET11d-rOnc (Q1, M23L, S72C) recombinant plasmid is then used to transform an E.coli BL21(DE3) host cell (FIG. 2, step 120) to express the new rOnc (Q1, M23L, S72C) target gene (FIG. 2, step 130). The expressed protein has an N-terminal methionine (Met) residue at position −1 followed by a residue of glutamine (Gln) at position 1. When the methionine residue is cleaved (FIG. 2, step 140) the glutamine autocyclizes to form pyroglutamic acid (<Glu), thereby forming cysteinized ranpirnase (SEQ ID NO:2).

Although at least one preferred embodiment of the invention has been described above, this description is not limiting and is only exemplary. The scope of the invention is defined only by the following claims:

What is claimed is:

1. A method of constructing an isolated nucleic acid encoding a protein having an N-terminal methionine residue at position −1 and a glutamine residue at position 1, said encoded protein, after its position −1 methionine residue has been cleaved and its glutamine residue has been autocyclized, being the Ribonuclease of SEQ ID NO:1 or the Ribonuclease of SEQ ID NO:2, comprising the following steps:
   starting with pET11d-rOnc(Q1, M23L) recombinant plasmid DNA;
   identifying a specific site-directed mutation of said DNA that must be carried out to produce an isolated nucleic acid encoding the Ribonuclease of SEQ ID NO:1 or the Ribonuclease of SEQ ID NO:2;
   using first and second PCR reactions in an overlapping PCR protocol to generate two overlapping nucleic acid fragments, each bearing said identified site-directed mutation within their regions of overlap; and
   using said two overlapping nucleic acid fragments in a third PCI reaction in the overlapping PCR protocol to generate an isolated nucleic acid encoding one of said proteins.

2. The method of claim 1, wherein the nucleic acid is cloned in a pET-11d vector, and wherein the PCR reactions comprise a forward PCR primer having an XbaI site and a reverse PCR primer having a stop codon and a BamHI site.

3. The method of claim 2, wherein the forward primer is SEQ ID NO:3 and the reverse PCR primer is SEQ ID NO:4.

4. The method of claim 2, wherein the desired end product is the Ribonuclease of SEQ ID NO:1, wherein the overlapping PCR protocol uses a mutated forward PCR primer and a mutated reverse PCR primer, wherein the mutated forward PCR primer is SEQ ID NO:5 and the mutated reverse PCR primer is SEQ ID NO:6.

5. The method of claim 2, wherein the desired end product is the Ribonuclease of SEQ ID NO:2, wherein the overlapping PCR protocol uses a mutated forward PCR primer and a mutated reverse PCR primer, wherein the mutated forward PCR primer is SEQ ID NO:7 and the mutated reverse PCR primer is SEQ ID NO:8.

6. The method of claim 1, further including the step of cloning the generated isolated nucleic acid as a gene into a vector.

7. The method of claim 6, further including the steps of using said vector to express a protei[008e] and cleaving an N-terminal methionine residue from said expressed protein and thereby allowing an adjacent glutamine residue to autocyclize into an N-terminal residue of pyroglutamic acid.

* * * * *

UNITED STATES PATENT AND TRADEMARK OFFICE
CERTIFICATE OF CORRECTION

PATENT NO. : 6,423,515 B1
DATED : July 23, 2002
INVENTOR(S) : Saxena

It is certified that error appears in the above-identified patent and that said Letters Patent is hereby corrected as shown below:

<u>Column 10,</u>
Lines 6-10, Claim 7 should read as follows:

7. The method of claim 6, further including the steps of using said vector to express a protein and cleaving an N-terminal methionine residue from said expressed protein and thereby allowing an adjacent glutamine residue to autocyclize into an N-terminal residue of pyroglutamic acid.

Signed and Sealed this

First Day of July, 2003

JAMES E. ROGAN
*Director of the United States Patent and Trademark Office*